United States Patent [19]
Whitney

[11] Patent Number: 5,939,596
[45] Date of Patent: *Aug. 17, 1999

[54] BUTADIENE REMOVAL SYSTEM FOR ETHYLENE PLANTS WITH FRONT END HYDROGENATION SYSTEMS

[75] Inventor: Mark Whitney, Houston, Tex.

[73] Assignee: Stone & Webster Engineering Corp., Boston, Mass.

[*] Notice: This patent is subject to a terminal disclaimer.

[21] Appl. No.: 09/006,076

[22] Filed: Jan. 12, 1998

Related U.S. Application Data

[63] Continuation of application No. 08/727,146, Oct. 8, 1996, Pat. No. 5,763,715.

[51] Int. Cl.[6] ................................................ C07C 5/03
[52] U.S. Cl. ........................ 585/259; 585/809; 585/810; 585/867; 585/258; 585/264
[58] Field of Search .................................. 585/809, 810, 585/867, 258, 259, 264

[56] References Cited

U.S. PATENT DOCUMENTS

| | | | |
|---|---|---|---|
| 1,948,777 | 2/1934 | Young et al. | 202/40 |
| 2,069,172 | 1/1937 | Miller | 196/13 |
| 2,088,887 | 8/1937 | Wagner | 196/10 |
| 2,376,425 | 5/1945 | Frey | 260/680 |
| 2,420,906 | 5/1947 | Packie et al. | 260/681 |
| 2,500,353 | 3/1950 | Gantt | 260/683 |
| 2,775,634 | 12/1956 | Nowlin | 260/677 |
| 2,813,920 | 11/1957 | Cobb, Jr. | 260/683 |
| 2,925,452 | 2/1960 | Broughton | 260/681 |
| 2,938,934 | 5/1960 | Williams | 260/677 |
| 2,970,177 | 1/1961 | Cobb, Jr. | 260/677 |
| 3,075,917 | 1/1963 | Kronig et al. | 208/255 |
| 3,293,316 | 12/1966 | Clay | 260/681 |
| 3,313,724 | 4/1967 | Kniel | 208/340 |
| 3,328,480 | 6/1967 | Begley et al. | 260/681 |
| 3,772,158 | 11/1973 | Sarno | 203/53 |
| 3,795,588 | 3/1974 | Preusser et al. | 203/25 |
| 3,798,132 | 3/1974 | Sarno | 203/53 |
| 4,020,114 | 4/1977 | Rescalli et al. | 260/681 |
| 4,038,156 | 7/1977 | Knott et al. | 203/45 |
| 4,049,742 | 9/1977 | Weitz et al. | 260/681 |
| 4,237,330 | 12/1980 | Lindner et al. | 585/807 |
| 4,266,086 | 5/1981 | Patel | 585/810 |
| 4,269,668 | 5/1981 | Patel | 203/9 |
| 4,292,141 | 9/1981 | Lindner et al. | 203/49 |
| 4,401,515 | 8/1983 | Arakawa et al. | 203/25 |
| 4,520,225 | 5/1985 | Marty et al. | 585/832 |
| 4,545,895 | 10/1985 | Brand et al. | 208/351 |
| 4,555,312 | 11/1985 | Ogura | 203/29 |
| 4,556,461 | 12/1985 | Ogura et al. | 203/29 |
| 4,596,655 | 6/1986 | van Eijl | 208/348 |
| 4,743,282 | 5/1988 | Mehra | 62/17 |
| 4,832,718 | 5/1989 | Mehra | 62/17 |
| 4,859,286 | 8/1989 | Kaibel et al. | 203/75 |
| 4,900,347 | 2/1990 | McCue, Jr. et al. | 62/24 |
| 5,019,143 | 5/1991 | Mehrta | 62/17 |
| 5,035,732 | 7/1991 | McCue, Jr. | 62/24 |
| 5,220,097 | 6/1993 | Lam et al. | 585/809 |
| 5,326,929 | 7/1994 | Mehra et al. | 585/809 |
| 5,387,731 | 2/1995 | Jenkins et al. | 585/259 |
| 5,414,170 | 5/1995 | McCue et al. | 585/264 |
| 5,502,971 | 4/1996 | McCarthy et al. | 62/20 |

*Primary Examiner*—Walter D. Griffin
*Assistant Examiner*—Tung Doan
*Attorney, Agent, or Firm*—Hedman, Gibson & Costigan, P.C.

[57] ABSTRACT

The present invention provides a process and system for the removal of butadiene from a cracked gas stream prior to entering a front end hydrogenation reactor in an olefin production facility.

9 Claims, 1 Drawing Sheet

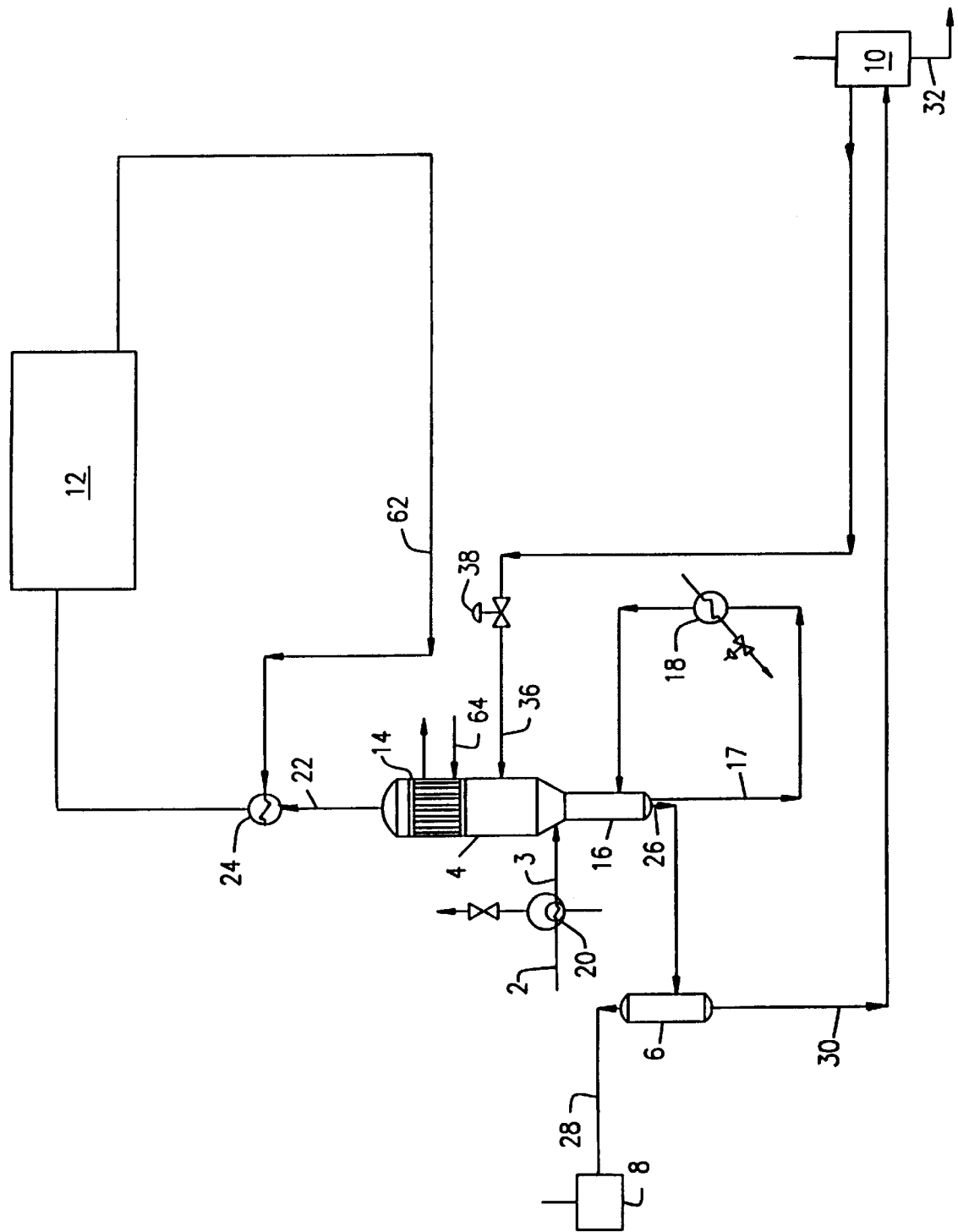

BUTADIENE REMOVAL SYSTEM FOR ETHYLENE PLANTS WITH FRONT END HYDROGENATION SYSTEMS

This is a continuation of application Ser. No. 08/727,146, filed Oct. 8, 1996, now U.S. Pat. No. 5,763,715.

FIELD OF INVENTION

This invention relates to a system for the removal of butadiene and heavier hydrocarbons from a cracked gas stream prior to entering a front end hydrogenation reactor in an olefin production facility.

BACKGROUND OF THE PRESENT INVENTION

In order to recover light mono-olefins, ethylene, propylene and butenes from a process gas stream containing other hydrocarbon constituents such as a cracked gas, the prior art has typically employed multi-stage rectification and cryogenic chilling trains. Especially successful processes have included McCue, Jr. et al. U.S. Pat. No. 4,900,347 and McCue, Jr. U.S. Pat. No. 5,035,732. In general these processes fall into two groups, one known as a "front-end" process, the other as a "tail-" or "back-end" process. In the front end process, a full-range stream containing both light and heavy components ranging from hydrogen up to C5's and heavier is processed over a fixed bed of selective hydrogenation catalyst. The catalyst is operated to effect complete removal of simple acetylene and removal of a majority of the methylacetylene and propadiene if present. A majority of the butadiene and dienes are also hydrogenated. The recovery of butadiene and heavier dienes upstream of the reactor system is important because of their commercial value and their tendency to foul the hydrogenation process when the heavy materials remain in the process stream.

In the tail-end process, the full range stream is first fractionated, followed by removal of acetylenes from the individual concentrated streams by reacting these alkynes with hydrogen over selective hydrogenation catalysts. Such a process increases capital cost and is energy-intensive.

In the past numerous methods have been employed to overcome the inefficiencies of these processes. For example, a distillation system can be used upstream of a front-end hydrogenation reactor. However, the distillation tower must function as a deethanizer or partial depropanizer in order to place enough $C_3$ material in the bottoms to lower the boiling point of the bottoms material below the temperature where $C_4$ and heavier dienes will polymerize and foul the tower reboiler. This requires the tower to be large in size, expensive due to its high pressure and low temperature construction and energy intensive.

Another method that has been employed is to sufficiently cool the stream at high pressure prior to the reactor to condense most of the butadiene and heavier hydrocarbons. The liquid is then distilled at low pressure (to avoid polymerization and fouling) to produce liquid containing $C_3$ and heavier material. However, the tower overhead vapors, which contain large quantities of light hydrocarbon material, must be recycled into the cracked gas compressor.

Still another method used in the prior art is to employ a back-end acetylene hydrogenation system with a deethanizer. This method removes butadiene before the hydrogenation reactor and with appropriate recycles and deethanizer operating conditions avoids $C_4$ and heavier diene polymerization. However, such a process requires large amounts of energy for hydrogen recovery and purification and deethanizing. Back end reactor systems typically require frequent regenerations to maintain selectivity and minimize the potential for runaway reactions.

By contrast, a front-end hydrogenation reactor provides cooler operating conditions because the gases are greatly diluted by the presence of hydrogen and methane. The front-end reactor also enables the hydrogen in the process stream to be used for hydrogenation, minimizes catalyst fouling so that frequent on-site catalyst regeneration is not required, minimizes green oil production, and provides ethylene and propylene gain across the reactor so that production from the plant is increased.

The use of a front-end reactor and a depropanizer or deethanizer as the front end column has been found to provide greater stability and flexibility for the operation of an ethylene plant, see McCue, Jr. U.S. Pat. No. 5,414,170, so that it may be employed over a range of feedstocks from ethane and propane to atmospheric gas oil and the system is less subject to turndown or composition changes resulting from the cyclical operation of the pyrolysis furnaces.

Accordingly, it would represent a notable advancement in the state of the art if a system were provided which economically removes butadiene and heavier dienes from a cracked gas process stream prior to hydrogenation in an olefin production plant. To this end, the present inventor has developed a butadiene and heavier diene removal system for ethylene plants with front end hydrogenation systems. The butadiene recoverable with this removal process has, in many applications, an economic value greater than the mono-olefins and may be processed into a variety of petrochemicals such as but not limited to butyl rubber, hexamethylene diamine, adipic acid, 1,4-butanediol, sulfolane and chloroprene.

SUMMARY OF THE INVENTION

It is an object of the present invention to provide the economical removal of butadiene and heavier dienes from a cracked gas process stream prior to hydrogenation in an olefin production plant.

It is another object of the present invention to provide an efficient system for providing a lower than normal acetylene reactor inlet temperature for initial start-up without the need to employ a front-end deethanizer or depropanizer.

It is still another object of the present invention to minimize the need to make adjustments in furnace operation to control CO make.

It is further an object of the present invention to provide a system for butadiene removal for ethylene plants that readily lends itself to ethane cracking ethylene plant designs including grassroots and revamp applications that value butadiene.

It is still another object of the present invention to provide a system for removal of butadiene using an internally generated $C_3$ stream, thereby avoiding the addition of an outside extraction solvent.

It is still a further object of the present invention to provide a source of butadiene for producing butadiene derivative petrochemicals.

Thus, in its broadest aspect the present invention provides an absorber tower for removal of butadiene and heavier hydrocarbons from a cracked gas stream. Absorber towers are well known to those of ordinary skill in the art. An absorbing liquid is passed through the tower to contact the cracked gas. Any absorbing liquid known to selectively absorb butadienes and heavier dienes may be employed. The absorber tower may run in co-current or countercurrent fashion and may be equipped with means for generating more than one stage of equilibrium, i.e, trays, packing and the like.

The absorber tower operates at the full cracked gas discharge pressure of a hydrocarbon processing system and is preferably located upstream of a front end hydrogenation system in an ethylene plant. The absorber tower is comprised of a condenser and a stripping section.

Preferably, the process of the present invention employs an internally generated $C_3$ stream delivered to the absorber tower wherein the butadiene is "washed" out of the cracked gas stream. The resultant absorber tower bottoms is a butadiene-containing liquid (which contains negligible amounts of ethylene) that is separated downstream at low pressure into useful products for further processing into petrochemicals. The overhead of the absorber tower containing the mono-olefins passes through the front end hydrogenation reactor for subsequent processing into component streams.

Compared to either back-end hydrogenation or front-end deethanizers, the equipment costs of the present invention are much lower. The absorber may handle the entire cracked gas stream at high pressure, moderate temperatures and has relatively few stages whereas the front-end deethanizer of the prior art must be much larger to handle the same flow run at much lower pressure and must be designed for colder temperature and has many more stages. The back-end hydrogenation system has expensive hydrogen purification and a large deethanizer tower. Furthermore, because the present invention recycles $C_3$ material into the reactor inlet, start-up of the reactor is simplified.

BRIEF DESCRIPTION OF THE DRAWINGS

The FIGURE depicts in flow chart format a preferred integrated system for the removal of butadiene according to the present invention.

DESCRIPTION OF THE PREFERRED EMBODIMENTS

The present invention, although having applications in processes wherein butadiene is to be removed from process streams, will be described in an ethylene processing system environment.

In a preferred embodiment a system is shown in FIGURE that includes absorber tower 4, separator drum 6, third stage suction drum 8, $C_2$ recycle tower 10 and front-end hydrogenation system 12.

The absorber tower 4 comprises essentially a condenser 14 and a stripper section 16. In addition, a reboiler loop 18 is provided to serve the absorber tower 4. Heat exchangers 20 and 24 are included in the absorber tower inlet line 3 and overhead discharge line 22 respectively.

Referring to the FIGURE, a dry cracked gas feedstream, such as obtained from a crude oil steam pyrolysis facility, in a line 2 is chilled in absorber feed chiller 20 using a refrigerant. The temperature of the refrigerant in the absorber feed chiller 20 is dependent on the composition and pressure of the feed, but in at least one embodiment the temperature is most preferably maintained at about 20 degrees F (−7 degrees C). The refrigerant is any appropriate refrigerant such as propylene.

The cooled feed from the feed chiller 20 passes through outlet line 3 to a packed or trayed absorber tower 4. The absorber tower 4 in the preferred embodiment has a condenser section 14 at the top and a stripping section 16 at the bottom. The cold side of the condenser section 14 is provided through a line 64 with a coolant such as propylene. The operating temperature of the condenser section 14 is dependent on the composition of feed introduced, however, in at least one embodiment the operating temperature is most preferably about −10 degrees F (−20 degrees C). The cooled feed is washed in absorber tower 4 by a $C_3$ reflux stream introduced via line 36 from a $C_2$ recycle tower 10 into the condenser section 14. The ratio of the flow of $C_3$ reflux to the cooled feed stream entering the absorber tower 4 is varied by valve 38 or any other conventional means for varying stream flow to control cracked gas butadiene content.

The vapor stream from the condenser section 14 of the absorber tower 4 containing a majority of the lighter components of the feedstream such as methane, ethylene, propylene, propane and acetylene, is withdrawn from the absorber tower 4 through a line 22. Desired withdrawal pressure and temperature conditions may vary depending on the makeup of the feedstream. The gas stream in the line 22 is subsequently heated in the feed/effluent exchanger 24 and optionally heated a second time to achieve optimum acetylene reactor feed temperature. Preferably, the feed/effluent exchanger 24 employs effluent from a downstream hydrogenation step to heat via a line 62 the gas stream in line 22. The heated cracked gas is then fed via the line 22 to an acetylene reactor system of a front end hydrogenation system 12.

The bottom stripping section 16 is employed to reduce $C_2$ content of the bottom product. In the absorber a majority of the heavier components are physically absorbed and proceed downwardly to the bottom stripping section 16 where they are removed in lines 17 and 26. The bottoms exiting through the line 17 are stripped in reboiler 18 and returned to the stripper section 16 of the absorber tower 4. In the preferred embodiment quench water is provided to supply reboil heat in the reboiler 18. The bottoms from the stripping section 16 is a butadiene containing liquid product, comprising substantially all of the $C_4$ components with some $C_2$ and $C_3$ components, which is withdrawn through the line 26 from the stripping section 16 of the absorber tower 4. The bottoms from the absorber tower 4 is letdown in pressure and passed via line 26 to the separator drum 6. A rich bottom liquid stream containing $C_3$ and heavier hydrocarbons including butadiene is withdrawn from the separator drum 6 and passed via line 30 to a $C_2$ recycle tower 10 of conventional design for separating a $C_2$ stream overhead, a $C_3$ side stream, and a $C_3$ plus bottoms stream 32 containing other products including butadiene. A resulting lean liquid side stream is withdrawn from the $C_2$ recycle tower 10 and recycled via line 36 as the $C_3$ reflux stream to absorber tower 4.

Flash vapor is withdrawn from the separator drum 6 and fed via line 28 to a third stage suction drum 8 for recovery or further processing.

The conditions employed in the front-end butadiene removal system according to the present invention can vary appreciably depending upon the compositional make-up and pressure of the stream being treated. $C_3$ reflux stream flow to the absorber tower 4 is at least sufficient for removing butadiene from a cracked gas stream. The process can be carried out employing a packed or trayed absorber tower or other means known to those skilled in the art.

Variations of the present invention will suggest themselves to those skilled in the art in light of the above-detailed description. All such variations and modifications are within the full intended scope of the appended claims. All of the above-referenced patents are hereby incorporated by reference.

What is claimed is:

1. A process for removing butadiene from a feed stream comprising the steps of
    (i) contacting the feed stream with an absorbent in an absorber tower to produce a vapor phase stream rich in $C_2$ and lighter material and a liquid phase stream rich in $C_3$ and heavier materials including butadiene;
    (ii) hydrogenating acetylenes in said vapor phase stream in a front-end hydrogenation reactor;
    (iii) separating said liquid phase stream in a second separation zone to produce a butadiene-rich liquid; and
    (iv) recovering butadiene from said second separation zone.

2. A process as defined in claim 1 wherein the feed stream is derived from the product stream of a steam pyrolysis facility.

3. A process as defined in claim 1 wherein the feed stream comprises butane, butenes, butadiene, propane, propylene, ethane, ethylene, methylacetylene, acetylene, methane, hydrogen, carbon monoxide and mixtures thereof.

4. A process as defined in claim 1 wherein the feed stream is chilled prior to entering said absorber tower.

5. A process as defined in claim 1 wherein said absorber tower comprises a top condenser section and a bottom stripping section.

6. A process as defined in claim 5 wherein said feed stream is fed to said top condenser section of said absorber tower.

7. A process as defined in claim 1 wherein said liquid phase stream is separated in said second separation stage to produce a second vapor phase stream and a second liquid phase stream.

8. A process as defined in claim 5 wherein said top condenser section operates at a temperature ranging from about −15 degrees F to about 5 degrees F.

9. A process for removing butadiene from a feed stream prior to entering a front-end hydrogenation reactor in an olefin production facility, comprising the steps of
    (i) chilling an olefin containing feed stream to cool and at least partially condense said feed stream;
    (ii) contacting said chilled olefin plant feed stream with an absorbent in an absorber tower comprising a top condenser section and a bottom stripping section to produce a vapor phase stream rich in $C_2$ and a liquid phase stream rich in $C_3$ and $C_4$ and comprising butadiene;
    (iii) hydrogenating the acetylenes in said vapor phase stream in a front-end hydrogenation reactor;
    (iv) heating said butadiene—containing liquid phase stream in said bottom stripping section of said absorber tower to reduce the $C_2$ content of said butadiene—containing liquid phase stream;
    (v) heating said butadiene—containing liquid phase stream in a second separation zone to produce a second liquid phase stream and a second vapor phase stream, said second liquid phase stream being rich in butadiene and $C_3$;
    (vi) recovering said butadiene—rich second liquid phase from said second separation zone;
    (vii) removing butadiene from said second liquid phase stream in a $C_2$ recycle tower; and
    (viii) recycling the $C_3$ stream to said top condenser section of said absorber tower to remove butadiene from said olefin plant feed stream.

* * * * *